(12) United States Patent
Heilman et al.

(10) Patent No.: US 8,672,871 B2
(45) Date of Patent: Mar. 18, 2014

(54) ENDOVASCULAR CEREBROSPINAL FLUID SHUNT

(75) Inventors: Carl Heilman, Wayland, MA (US); Adel M. Malek, Lexington, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 13/569,212

(22) Filed: Aug. 8, 2012

(65) Prior Publication Data

US 2012/0296256 A1     Nov. 22, 2012

Related U.S. Application Data

(62) Division of application No. 12/362,152, filed on Jan. 29, 2009, now abandoned.

(51) Int. Cl.
*A61M 1/00* (2006.01)
*A61M 25/00* (2006.01)
*A61M 25/10* (2013.01)

(52) U.S. Cl.
USPC ....... 604/8; 604/9; 604/10; 623/1.1; 623/1.24

(58) Field of Classification Search
USPC ............... 604/8, 9, 10, 540, 541, 93.01, 264; 623/4.1, 5.11, 6.64
See application file for complete search history.

(56) References Cited

U.S. PATENT DOCUMENTS

| | | | |
|---|---|---|---|
| 4,413,985 A * | 11/1983 | Wellner et al. | 604/9 |
| 4,474,569 A * | 10/1984 | Newkirk | 604/8 |
| 4,475,898 A * | 10/1984 | Brodner et al. | 604/9 |
| 4,631,051 A * | 12/1986 | Harris | 604/9 |
| 4,737,153 A | 4/1988 | Shimamura et al. | |
| 4,950,232 A | 8/1990 | Ruzicka et al. | |
| 5,000,731 A * | 3/1991 | Wong et al. | 604/8 |
| 5,385,541 A | 1/1995 | Kirsch et al. | |
| 5,405,316 A | 4/1995 | Magram | |
| 5,851,199 A | 12/1998 | Peerless et al. | |
| 6,126,628 A | 10/2000 | Nissels | |
| 6,190,353 B1 * | 2/2001 | Makower et al. | 604/95.01 |
| 6,283,934 B1 | 9/2001 | Borgesen | |
| 6,579,311 B1 * | 6/2003 | Makower | 623/1.23 |
| 2002/0188308 A1 * | 12/2002 | Tu et al. | 606/167 |
| 2003/0135147 A1 | 7/2003 | Rosenberg et al. | |
| 2003/0220604 A1 * | 11/2003 | Al-Anazi | 604/9 |
| 2004/0059280 A1 * | 3/2004 | Makower et al. | 604/8 |
| 2004/0087887 A1 * | 5/2004 | Nilsson | 604/8 |
| 2004/0236309 A1 | 11/2004 | Yang | |
| 2005/0137646 A1 * | 6/2005 | Wallace et al. | 607/45 |
| 2005/0245906 A1 | 11/2005 | Makower et al. | |
| 2005/0256510 A1 | 11/2005 | Moskowitz et al. | |
| 2006/0015152 A1 * | 1/2006 | Wallace | 607/45 |
| 2006/0224101 A1 * | 10/2006 | Glenn | 604/8 |

(Continued)

*Primary Examiner* — Adam Marcetich
(74) *Attorney, Agent, or Firm* — Occhiuti & Rohlicek LLP

(57) ABSTRACT

An implantable shunt device for draining cerebrospinal fluid from a patient's subarachnoid space includes a shunt having opposed first and second ends and a one-way valve located at the first end of the shunt. A hollow passageway extends between the tip and one-way valve such that fluid can be drained through the tip and out through the valve. The endovascular cerebrospinal fluid shunt of the present invention can be placed into a patient percutaneously via a catheter inserted into the venous system of the body through a needle hole, without the need for open surgery. The device allows for more physiologic drainage of cerebrospinal fluid since the device shunts cerebrospinal fluid into the same cerebral venous system that occurs naturally in normal people.

18 Claims, 5 Drawing Sheets

(56) References Cited

U.S. PATENT DOCUMENTS

| | | |
|---|---|---|
| 2007/0112291 A1 | 5/2007 | Borgesen |
| 2007/0179426 A1* | 8/2007 | Selden .............................. 604/8 |
| 2007/0179428 A1* | 8/2007 | Kralick et al. .................... 604/9 |
| 2007/0276316 A1* | 11/2007 | Haffner et al. .................... 604/8 |
| 2008/0125805 A1* | 5/2008 | Mische ......................... 606/196 |
| 2009/0017098 A1 | 1/2009 | Di Bartolomeo |
| 2009/0076357 A1* | 3/2009 | Purdy ........................... 600/347 |
| 2010/0222732 A1* | 9/2010 | Sevrain ............................. 604/8 |

\* cited by examiner

ENDOVASCULAR CEREBROSPINAL FLUID SHUNT

CROSS-REFERENCE TO RELATED APPLICATIONS

This application is a divisional application of U.S. patent application Ser. No. 12/362,152 filed on Jan. 29, 2009, the contents of which are incorporated herein by reference in its entirety.

BACKGROUND OF THE INVENTION

1. Field of the Invention

The present invention relates to an endovascular shunt implantable into the wall of a patient's sigmoid sinus, and more particularly, to a shunt capable of draining cerebrospinal fluid from the patient's subarachnoid space to the venous system.

2. Description of the Related Art

It is known to treat hydrocephalus by draining cerebrospinal fluid (CFS) from the brain with a drain tube, catheter or shunt. See U.S. Pat. Nos. 5,385,541 and 4,950,232. These known devices are complex and invasive. The risk for infection is also increased due to the complexity of these devices.

The known shunts are limited to areas of placement due to fluid flow control. Moreover, the known shunts and methods of placements do not work in conjunction with a body's natural disease control processes. Accordingly, in recent years exploration of placement of a catheter or shunt in the venous sinus of a patient has been explored. See U.S. Pat. No. 6,283,934 and Published Application No. 2005/0256510.

However, fluid flow still poses difficulties due to the complexity of the devices and the placement areas. Commonly, the shunts/catheters are placed through the skull of the patient requiring pressure control to facilitate CSF flow and also creating a dangerous infection site.

Thus, there is a need for an endovascular shunt that can be inserted into the venous system percutaneously.

SUMMARY OF THE INVENTION

The present invention relates to an endovascular CSF shunt that drains CSF from the cistern around the cerebellum into the sigmoid sinus lumen.

The present invention also relates to a method of draining CSF by inserting, deploying and detaching the shunt of the present invention by an endovascular route through the venous system. The venous system is accessed either through the femoral vein or the jugular vein percutaneously.

The endovascular cerebrospinal fluid shunt of the present invention is an improvement over the standard cerebrospinal fluid shunts because it can be placed into a patient percutaneously via a catheter inserted into the venous system of the body through a needle hole, without the need for open surgery and the skin incisions required with current shunt devices. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

One aspect of the present invention is to provide an implantable shunt device for draining fluid from a patient's subarachnoid space. The device includes a shunt having opposed first and second ends. A one-way valve is located at the first end of the shunt and a helical tip is disposed at the second end. The helical tip penetrates the sigmoid sinus wall of the patient and a hollow passageway extending between the helical tip and the CSF cistern allows the CSF to be drained through the helical tip and out through the valve.

Another aspect of the present invention provides a method for draining cerebrospinal fluid from a patient's subarachnoid space, the method includes the steps of providing a shunt having opposed first and second ends, delivering the shunt to the sinus wall, implanting the helical tip in the sinus wall of the patient; and draining cerebrospinal fluid from the patient.

These and other features, aspects, and advantages of the present invention will become more apparent from the following detailed description of the preferred embodiment relative to the accompanied drawings, in which:

DETAILED DESCRIPTION OF THE PREFERRED EMBODIMENT

Figure 1:
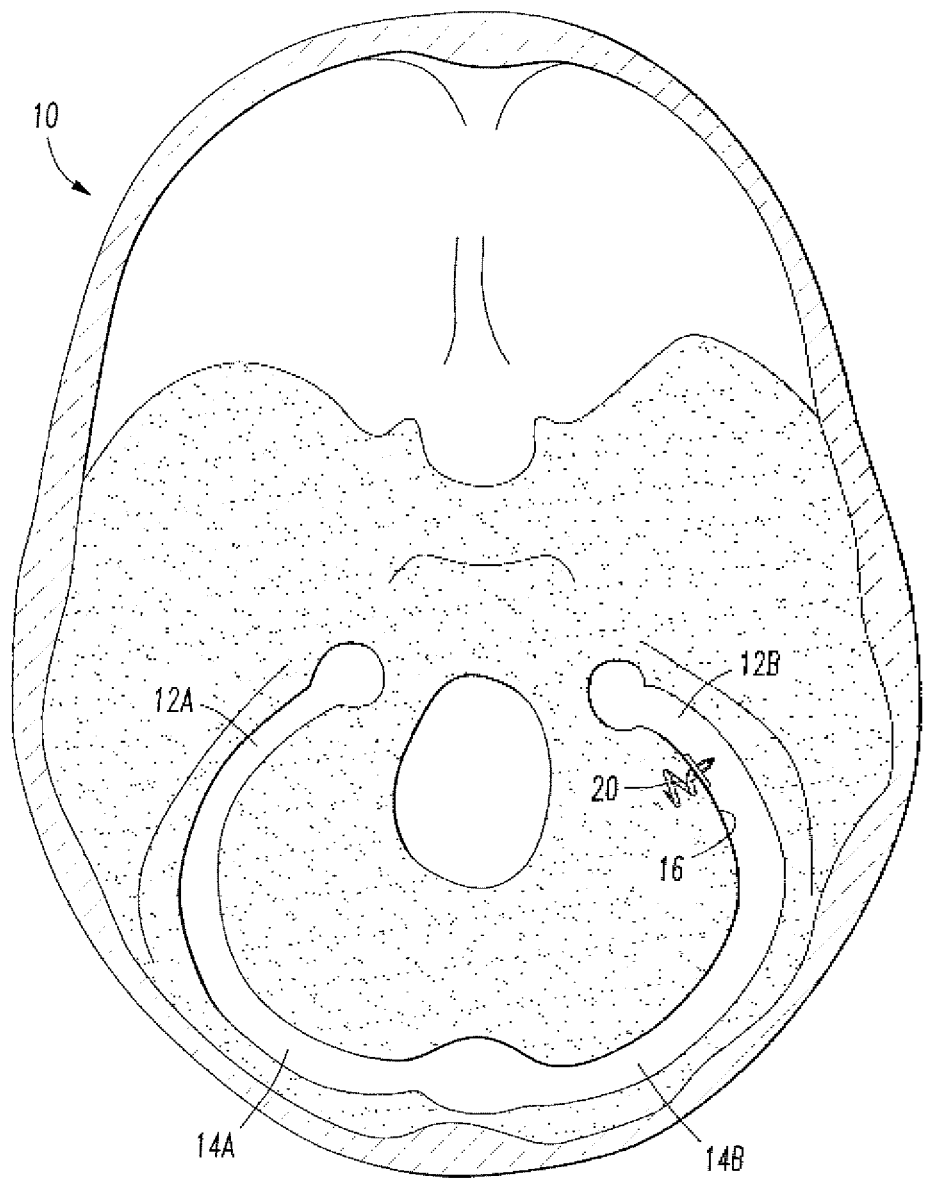
FIG. 1 is a top cross-sectional view of a human skull illustrating the placement of the shunt of the present invention.

Referring to FIG. 1, the endovascular shunt device of the present invention can be delivered to the right or left sigmoid sinus 12A, 12B of a patient's skull 10 via either the right or left jugular vein respectively of the venous system. The sigmoid sinus lumen 12 is located between the temporal bone (FIGS. 3-5) and the cerebellum.

A shunt 20 is implanted into a sigmoid sinus wall 16, so that one end communicates with CSF located in the cistern or CSF space 18 around the cerebellum 19. The device of the present invention uses the body's natural disease control mechanisms by delivering the CSF from cistern 18 into sigmoid sinus lumen 12 of the venous system. The venous system of the patient can be accesses either through the femoral or jugular veins (not shown) percutaneously. It should be appreciated that the shunt device of the present invention can be delivered to the sigmoid sinus via other locations.

Figure 2:
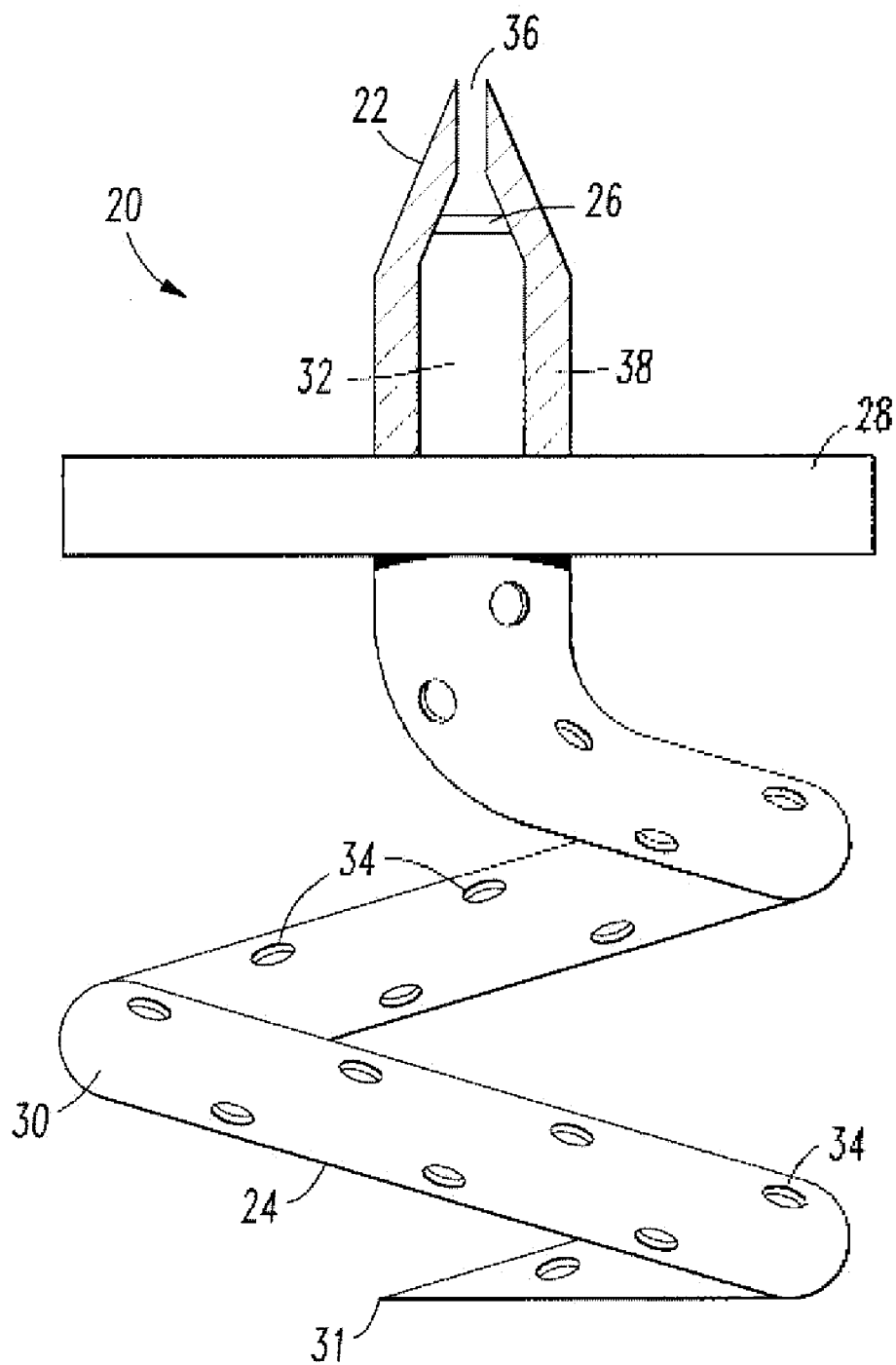
FIG. 2 is a partial cross-section of an embodiment of the endovascular shunt of the present invention.

As shown in FIG. 2, one embodiment of the endovascular CSF shunt 20 of the present invention includes opposed first and second ends 22, 24. A one-way valve 26 is located at first end 22. As will be described further herein, CSF can travel through shunt 20 and out end 22, however, other fluid cannot enter the shunt from open end 22.

A helical tip 30 is located at second end 24. As will be described further herein, helical tip 30 has a closed sharpened end 31 that is adapted to penetrate sinus wall 16. Tip 30 includes a plurality of apertures 34 through which the CSF enters the tip. A hollow passageway 32 extends from tip 30 and open end 22, such that the CSF fluid entering through apertures 34 can pass through valve 26 and pass from an outlet 36.

Figure 3:
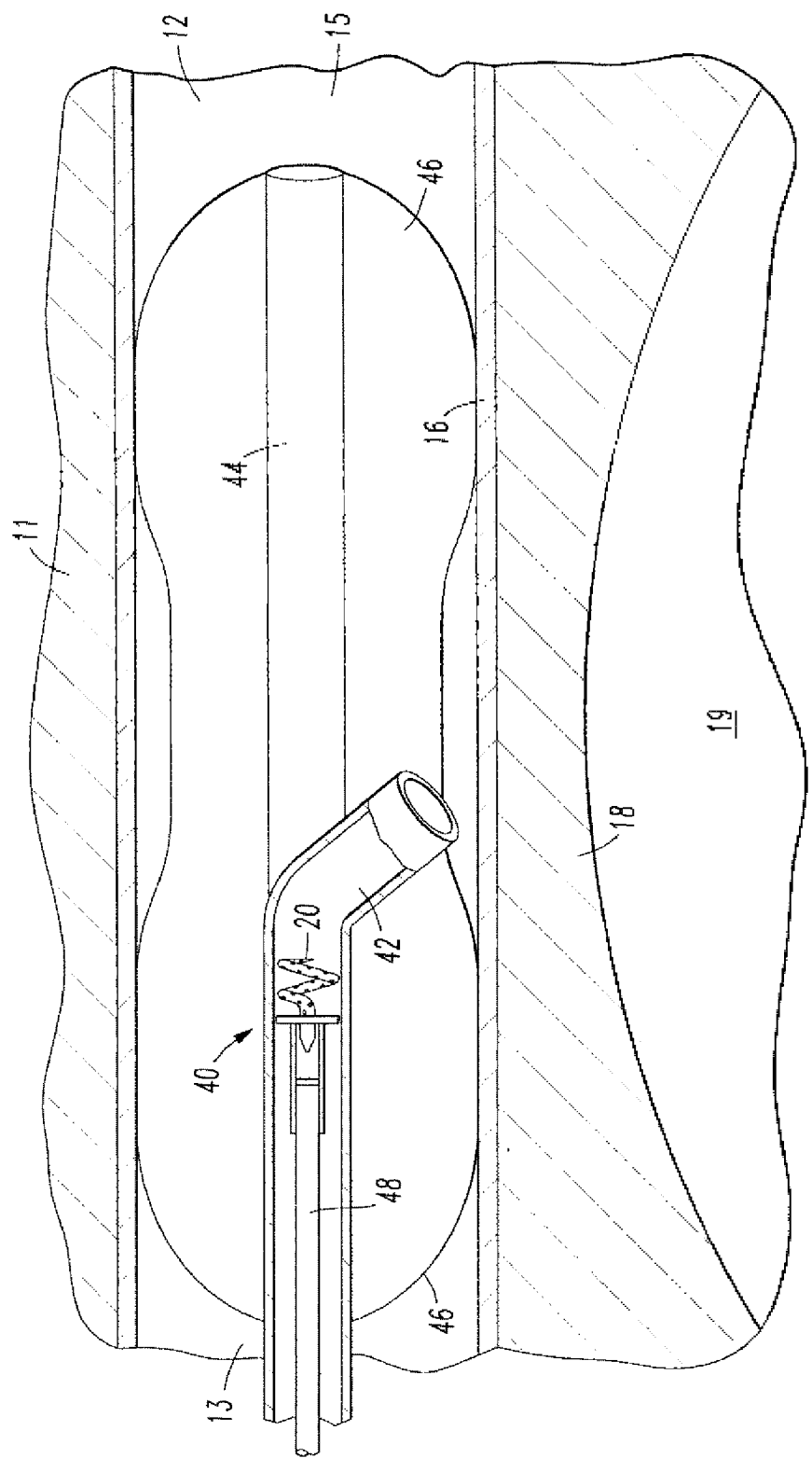
FIG. 3 is a partial view of delivering the endovascular shunt of the present invention to the CSF space of a patient's venous system.
Figure 4:
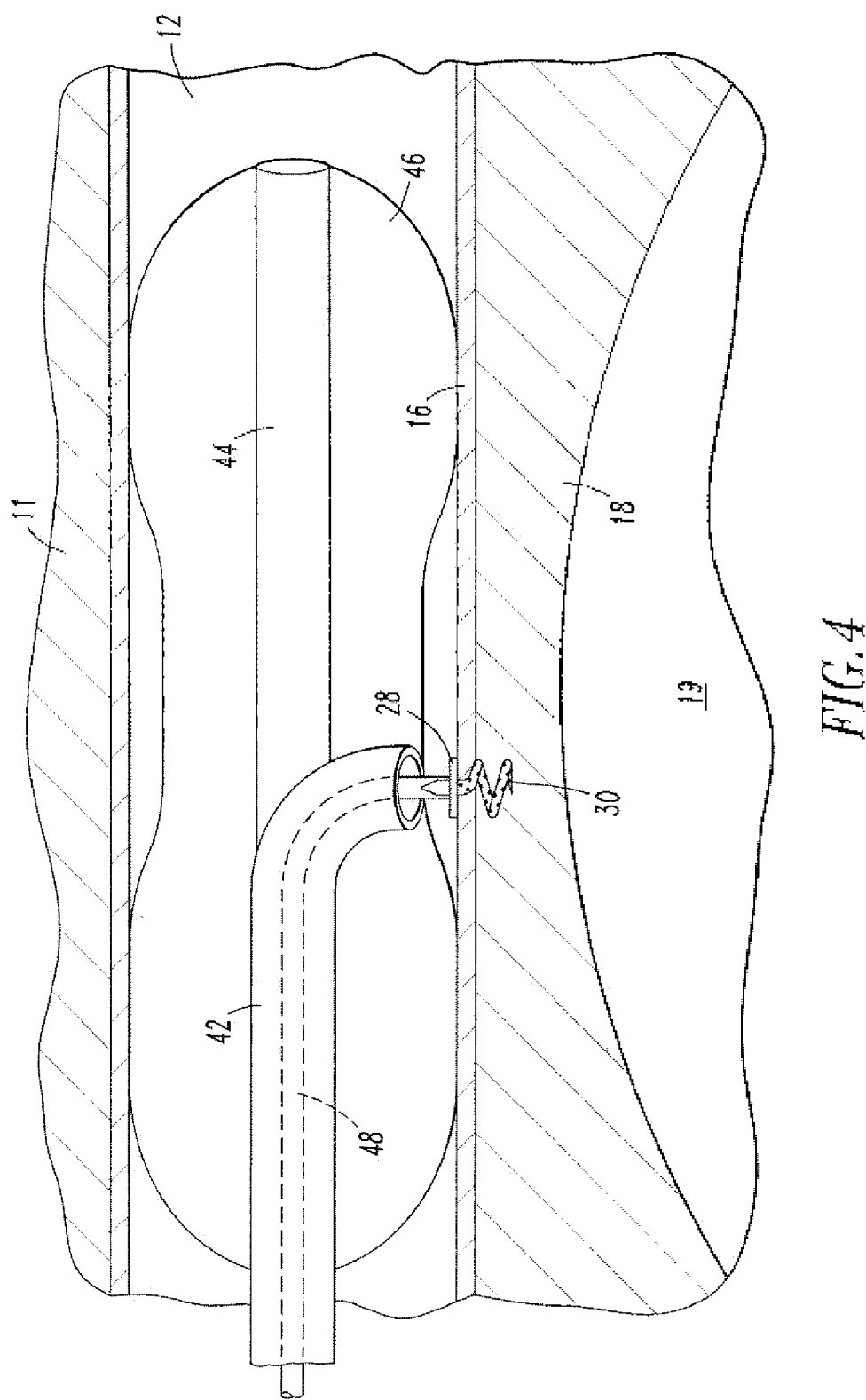
FIG. 4 is a partial view of the implantation of the endovascular shunt of the present invention into the sigmoid sinus wall.
Figure 5:
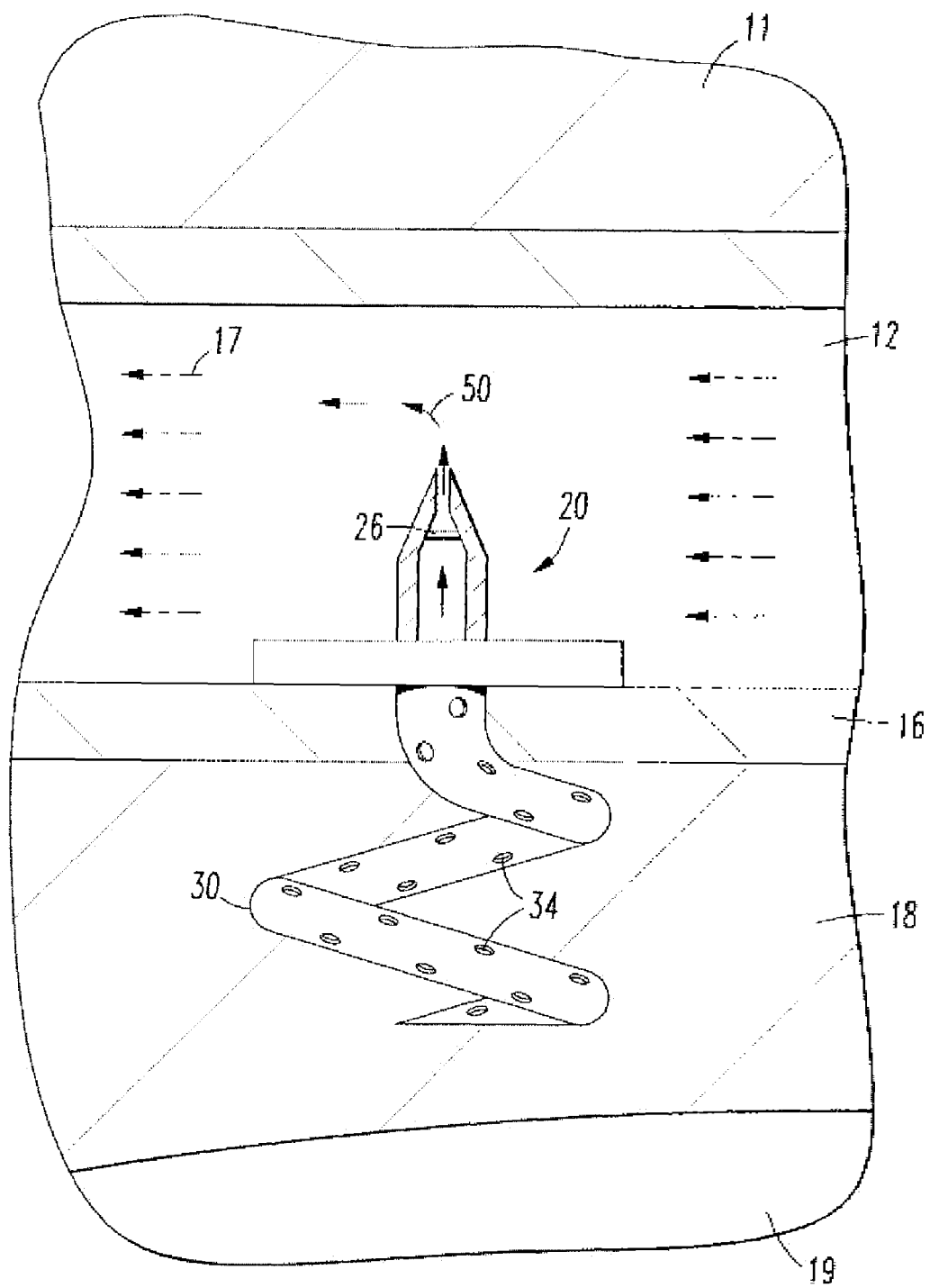
FIG. 5 is a partial view of the endovascular shunt of the present invention implanted in the sigmoid sinus wall.

Referring to FIGS. 3-5 and as described above, a delivery catheter 40 is delivered to the venous system via the femoral or jugular vein. Catheter 40 is inserted into sigmoid sinus lumen 12 at a proximal location 13 toward the neck and inserted toward a distal end 15, which is toward the brain.

Delivery catheter 40 includes a second lumen 44 and a shunt delivery port 42. Lumen 44 directs the entire catheter to the correct location with for example, a guide wire, to allow injection of intravenous contrast to visualize the venous lumen. Lumen 44 also supports balloons 46 that can be deployed to occlude venous flow during stunt implantation. Shunt 20 is positioned at an end of an internal catheter 48 that is manipulated through catheter 40 and port 42. To prevent thrombosis within the sigmoid sinus and around the endovascular shunt, shunt 20 can be provided with an antithrombic coating 38

As shown in FIG. 4, internal catheter 48 facilitates twisting of shunt 20 so that it penetrates through sigmoid sinus wall 12. Catheter 48 includes a hollow lumen to allow CSF withdrawal after shunt penetration of the sigmoid sinus wall to confirm that CSF is flowing through the shunt. However, it must be rigid enough to allow twisting of the shunt such that it penetrates the sigmoid sinus wall. Upon insertion, helical tip 30 extends into cistern 18 and CSF located therein. A projection 28 located on shunt 20 between the ends abuts the wall and prevents the shunt from passing therethrough. Upon placement, internal catheter 48 is detached. The CSF can also be aspirated back prior to detachment of catheter 48.

Thereafter, delivery catheter 40 can be removed and shunt 20 is implanted as shown in FIG. 5. CSF 50 draining from outlet 36 from CSF space 18 is delivered to the venous blood flow 17 and removed. It should be appreciated that other means of fluid removal can communicate with shunt 20 to direct the CSF as desired. It also should be appreciated that shunt 20 can incorporate different tips at end 24.

Thus, the endovascular cerebrospinal fluid shunt of the present invention can be placed into a patient percutaneously via a catheter inserted into the venous system of the body through a needle hole, without the need for open surgery and the skin incisions required with current shunt devices. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

The invention claimed is:

1. A method for draining cerebrospinal fluid from a patient's subarachnoid space into the venous system, the method comprising: providing a shunt having opposed first and second ends, a one-way valve located at the first end of the shunt, and a tip disposed at the second end, said tip being constructed to penetrate the dural cerebral venous sinus wall into the subarachnoid space, from within the lumen of the venous sinus of the patient, wherein the first and second ends are in fluid communication to enable the cerebrospinal fluid to be drained through the tip and out through the valve into the venous system; delivering the shunt to the sigmoid sinus wall via a catheter using an endovascular approach; implanting the tip through the cerebral venous sinus wall of the patient; and draining cerebrospinal fluid from the patient's subarachnoid space into the patient's venous system.

2. The method of claim 1, further comprising: placing the shunt percutaneously into the venous system of the patient without the need for open surgery.

3. The method of claim 1, wherein the cerebrospinal fluid is drained from the patient's subarachnoid space.

4. The method of claim 3, wherein the cerebrospinal fluid is drained into the cerebral venous system of the patient.

5. The method of claim 3, wherein the cerebrospinal fluid is drained into a cerebral venous sinus lumen of the patient.

6. The method of claim 1, wherein the shunt further comprises a projection between said first and second ends.

7. The method of claim 6, further comprising: abutting the projection against the sinus wall.

8. The method of claim 1, wherein the tip has a sharpened end disposed at the second end.

9. The method of claim 8, further comprising: penetrating the sinus wall of the patient with the sharpened end.

10. The method of claim 1, further comprising delivering the shunt to the cerebral venous sinus wall via a needle hole.

11. The method of claim 1, further comprising delivering the shunt to the cerebral venous sinus wall via the jugular vein.

12. The method of claim 11, wherein delivering the shunt to the cerebral venous sinus wall via the jugular vein includes delivering through the femoral vein.

13. The method of claim 1, further comprising delivering the shunt to the cerebral venous sinus wall via the femoral vein.

14. The method of claim 1, further comprising, after delivery of the shunt to the cerebral venous wall, removing the catheter from the patient.

15. The method of claim 1, further comprising providing the catheter with a hollow lumen to allow cerebrospinal fluid withdrawal through the shunt.

16. The method of claim 1, wherein delivering the shunt to the cerebral venous sinus wall is without open surgery.

17. The method of claim 1, wherein delivering the shunt to the cerebral venous sinus wall is without general anesthesia.

18. A method for draining cerebrospinal fluid from a patient's subarachnoid space into the venous system, the method comprising the steps of:
   providing a shunt having opposed first and second ends, a one-way valve located at the first end of the shunt, and a tip disposed at the second end, said tip being constructed to penetrate the cerebral venous sinus wall into the subarachnoid space, from within the lumen of the venous sinus of the patient, wherein the first and second ends are in fluid communication to enable the cerebrospinal fluid to be drained through the tip and out through the valve into the venous system;
   delivering the shunt to the sigmoid sinus wall via the jugular vein using an endovascular approach;
   implanting the tip through the cerebral venous sinus wall of the patient; and
   draining cerebrospinal fluid from the patient's subarachnoid space into the patient's venous system.

* * * * *